United States Patent [19]

Katakami et al.

[11] Patent Number: 4,639,451

[45] Date of Patent: Jan. 27, 1987

[54] PYRIDAZINONE DERIVATIVES

[75] Inventors: Tsutomu Katakami; Nobuyuki Fukazawa, both of Yokohama; Hajime Iizuka, Hiratsuka; Takashi Nishina, Mobara; Joji Kamiya, Mobara; Yasuhito Tanaka, Mobara; Takuo Nakano, Yokohama, all of Japan

[73] Assignee: Mitsui Toatsu Kagaku-Kabushiki Kaisha, Tokyo, Japan

[21] Appl. No.: 504,039

[22] PCT Filed: Oct. 20, 1982

[86] PCT No.: PCT/JP82/00415
§ 371 Date: Jun. 3, 1983
§ 102(e) Date: Jun. 3, 1983

[87] PCT Pub. No.: WO83/01447
PCT Pub. Date: Apr. 28, 1983

[30] Foreign Application Priority Data

Oct. 20, 1981 [JP] Japan .................. 56-166437
Oct. 20, 1981 [JP] Japan .................. 56-166438
Dec. 28, 1981 [JP] Japan .................. 56-209937

[51] Int. Cl.[4] .................. C07D 237/04; A61K 31/50
[52] U.S. Cl. .................. 514/247; 514/252; 544/238; 544/239
[58] Field of Search .......... 544/238, 239; 424/250; 514/247, 252

[56] References Cited

U.S. PATENT DOCUMENTS 3,806,509  4/1974  Lebkuecher et al. .......... 544/239
4,544,562  10/1985 Rossy et al. .................. 514/247

FOREIGN PATENT DOCUMENTS 2304977  8/1974  Fed. Rep. of Germany .
0046966  3/1982  Japan .

Primary Examiner—Nicholas S. Rizzo
Attorney, Agent, or Firm—Birch, Stewart, Kolasch & Birch

[57] ABSTRACT

This invention relates to pyridazinone derivatives of the general formula:

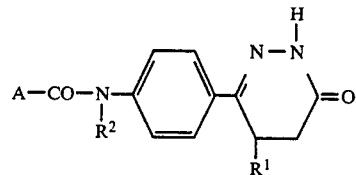

[wherein $R^1$ stands for a hydrogen atom or a lower alkyl group; $R^2$ for a hydrogen atom or a lower alkyl group; and A for (i) a ring selected from a benzene ring, a furan ring, a thiophene ring and a pyridine ring (on which ring 1-3 substituents or atoms selected from amino groups, nitro groups, lower alkanoylamino groups, hydroxyl groups, lower alkanoyloxy groups, sulfamoyl groups and halogen atoms may be present), or (ii) a grouping of the formula:

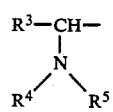

(wherein $R^3$ stands for a hydrogen atom, a lower alkyl group, a phenyl(lower)alkyl, a hydroxyphenyl(lower)alkyl group, a lower alkylmercapto(lower)alkyl group, a benzylmercapto(lower)alkyl group, a guanidino(lower)alkyl group, a nitroguanidino(lower)alkyl group, an indolyl(lower)alkyl group, a carbamoyl(lower)alkyl group or a carboxy(lower)alkyl group, $R^4$ for a hydrogen atom or a lower alkyl group, $R^5$ for a hydrogen atom, a lower alkyl group, a lower alkanoyl group, a benzoyl or a benzyloxycarbonyl group, and $R^3$ and $R^4$ may be combined to form a grouping of the formula:

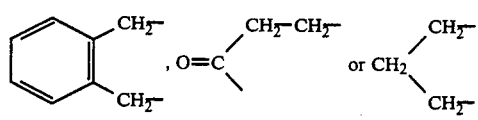

which forms a ring), or (iii) a grouping of the formula:

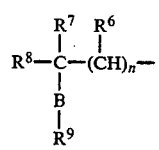

(wherein $R^6$, $R^7$ and $R^8$ each stand for a hydrogen atom or a lower alkyl group, B is an oxygen atom or a sulfur atom, $R^9$ stands for a hydrogen atom or a lower alkanoyl group, and n is 0 or 1)].

22 Claims, No Drawings

PYRIDAZINONE DERIVATIVES

TECHNICAL FIELD

The present invention relates to new substances, namely 6-(4-acylaminophenyl)-4,5-dihydro-3(2H)-pyridazinone derivatives.

Hitherto, dihydropyridazinone compounds, for example, 6-[p-(2-chloropropionylamino)-phenyl]-5-methyl-4,5-dihydropyridazone-(3) have known as substances possessing blood pressure depressing activity and platelets aggregation inhibiting activity (Japanese Laid-open Patent Appln. No. Sho-54-9289 referred to). These substances are recognized to be useful as medicaments for the remedy of diseases of circulatory organs, such as blood pressure depressing agents and anti-thrombotic agents. Development of further pharmacological usefulness is still expected for these substances.

The new pyridazinone derivatives concerned with the present invention are also new substances possessing pharmacological effects such as myocardial-contraction reinforcing activity in addition to blood pressure depressing activity and platelet aggregation inhibiting activity, and are very useful as medicaments for ciruclatory organs, such as blood pressure depressants, anti-thrombotic agents and medicines for the remedy of heart diseases, or as intermediates for these medicaments.

DISCLOSURE OF INVENTION

The present invention provides as new chemical substances pyridazinone derivatives of the general formula:

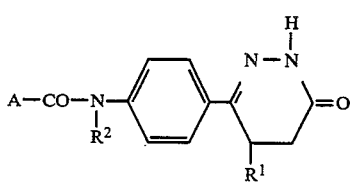   (I)

[wherein $R^1$ stands for a hydrogen atom or a lower alkyl group; $R^2$ for a hydrogen atom or a lower alkyl group; and A for (i) a ring selected from a benzene ring, a furan ring, a thiophene ring and a pyridine ring (on which ring 1–3 substituents or atoms selected from amino groups, nitro groups, lower alkanoylamino groups, hydroxyl groups, lower alkanoyloxy groups, sulfamoyl groups and halogen atoms may be present), or (ii) a grouping of the formula:

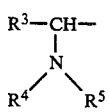

(wherein $R^3$ stands for a hydrogen atom, a lower alkyl group, a phenyl(lower)alkyl, a hydroxyphenyl(lower)alkyl group, a lower alkylmercapto(lower)alkyl group, a benzylmercapto(lower)alkyl group, a guanidino(lower)alkyl group, a nitroguanidino(lower)alkyl group, an indolyl(lower)alkyl group, a carbamoyl(lower)alkyl group or a carboxy(lower)alkyl group, $R^4$ for a hydrogen atom or a lower alkyl group, $R^5$ for a hydrogen atom, a lower alkyl group, a lower alkanoyl group, a benzoyl or a benzyloxycarbonyl group, and $R^3$ and $R^4$ may be combined to form a grouping

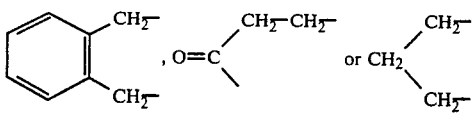

which forms a ring) or (iii) a grouping of the formula:

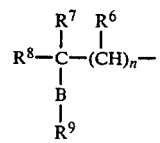

(wherein $R^6$, $R^7$ and $R^8$ each stand for a hydrogen atom or a lower alkyl group, B is an oxygen atom or a sulfur atom, $R^9$ stands for a hydrogen atom or a lower alkanoyl group, and n is 0 or 1)].

In the definitions for each notation given for the above general formula (I), the lower alkyl group means an alkyl group with 1–4 carbon atoms. Mentioned, for example, are methyl, ethyl, propyl, isopropyl, n-butyl, isobutyl, secbutyl or tert.-butyl groups. Examples of the lower alkanoyl group in the definitions for each notation given above include formyl, acetyl, propanoyl and butanoyl groups.

In compounds of the general formula (I), those in which A stands for (i) can be prepared by reacting a compound of the general formula:

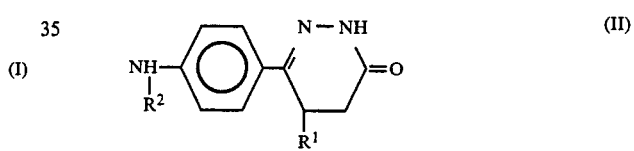   (II)

(wherein $R^1$ stands for a hydrogen atom or a lower alkyl group with 1–4 carbon atoms and $R^2$ for a hydrogen atom or a lower alkyl group with 1–4 carbon atoms), with a carboxylic acid of the general formula:

A—COOH   (III)

[wherein A stands for a ring selected from a benzene ring, a furan ring, a thiophene ring and a pyridine ring (on which ring 1–3 substituents or atoms selected from amino groups, nitro groups, lower alkanoylamino groups, hydroxyl groups, lower alkanoyloxy groups, sulfamoyl groups and halogen atoms may be present)], or a reactive functional derivative thereof.

Examples of the carboxylic acid of the general formula (III) include salicylic acid, acetylsalicylic acid, m-hydroxybenzoic acid, p-hydroxybenzoic acid, o-acetylaminobenzoic acid, o-aminobenzoic acid, m-aminobenzoic acid, p-aminobenzoic acid, m-acetaminobenzoic acid, p-acetaminobenzoic acid, o-nitrobenzoic acid, m-nitrobenzoic acid, p-nitrobenzoic acid, p-chlorobenzoic acid, p-bromobenzoic acid, o-chlorobenzoic acid, o-bromobenzoic acid, m-chlorobenzoic acid, m-bromobenzoic acid, 2,4-dichlorobenzoic acid, 2,4-dichloro-5-sulfamoylbenzoic acid and 4-chloro-3-sulfamoylbenzoic acid, 2-furancarboxylic acid, 3-furancarboxylic acid, 2-thiophenecarboxylic acid, 3-thiophenecarboxylic acid, 2-pyridinecarboxylic acid, 3-pyridinecarboxylic acid and 4-pyridinecarboxylic acid.

Acid halides such as acid chlorides, acid bromides or the like acid halides are preferably used as the reactive functional derivative of the carboxylic acids of the general formula (III). Besides these, acid anhydrides, mixed acid anhydrides such as a mixed acid anhydride with a monoalkyl carbonate, and active esters such as a p-nitrophenyl ester, a 2,4,5-trichlorophenyl ester, an N-phthalimide ester and an N-oxysuccinimide ester can also be used.

In case a compound of the general formula (II) is reacted with a carboxylic acid of the general formula (III) or a reactive functional derivative thereof a proper solvent is selectively used and the reaction is preferably carried out within a temperature range from room temperature to the boiling point of the reaction mixture. Preferable examples of the solvent include benzene, toluene, methylene chloride, chloroform, ether, tetrahydrofuran, dimethylformamide, and dimethylsulfoxide. If appropriate, the reaction can be carried out in the absence of such solvent. If necessary, a suitable acid-binding agent such as pyridine, triethylamine or the like organic base or an inorganic base, for example, potassium carbonate or sodium carbonate may be used for the reaction.

The above mentioned mixed acid anhydrides can be prepared by reacting the above carboxylic acid with an alkyl chlorocarbonate such as isobutyl chloroformate in a solvent such as dichloromethane, tetrahydrofuran, ethyl acetate, dimethylformamide or dimethylsulfoxide. When the mixed acid anhydride is prepared, a compound of the general formula (II) alone or optionally dissolved in a solvent may be added to the reaction mixture to effect reaction.

Examples of the compounds thus obtained are as follows:
6-[4-(2-hydroxybenzoylamino)-phenyl]-5-methyl-4,5-dihydro-3(2H)-pyridazinone,
6-[4-(2-hydroxybenzoylamino)-phenyl]-4,5-dihydro-3(2H)-pyridazinone,
6-[4-(3-hydroxybenzoylamino)-phenyl]-4,5-dihydro-3(2H)-pyridazinone,
6-[4-(4-hydroxybenzoylamino)-phenyl]-5-methyl-4,5-dihydro- 3(2H)-pyridazinone,
6-[4-(2-acetoxybenzoylamino)-phenyl)-5-methyl-4,5-dihydro-3(2H)-pyridazinone,
6-[4-(4-acetoxybenzoylamino)-phenyl]-5-methyl-4,5-dihydro-3(2H)-pyridazinone,
6-[4-(2-butanoyloxybenzoylamino)-phenyl]-5-methyl-4,5-dihydro-3(2H)-pyridazinone,
6-[4-(2-hydroxy-4-aminobenzoylamino)-phenyl]-5-methyl-4,5-dihydro-3(2H)-pyridazinone,
6-[4-(3-nitrobenzoylamino)-phenyl]-5-methyl-4,5-dihydro-3(2H)-pyridazinone,
6-[4-(2-aminobenzoylamino)-phenyl]-5-methyl-4,5-dihydro-3(2H)-pyridazinone,
6-[4-(2-acetylaminobenzoylamino)-phenyl]-5-methyl-4,5-dihydro-3(2H)-pyridazinone,
6-[4-(3-aminobenzoylamino)-phenyl]-5-methyl-4,5-dihydro-3(2H)-pyridazinone,
6-[4-(2-aminobenzoylamino)-phenyl]-4,5-dihydro-3(2H)-pyridazinone,
6-[4-(2,4-dichlorobenzoylamino)-phenyl]-4,5-dihydro-3(2H)-pyridazinone,
6-[4-(2,4-dichlorobenzoylamino)-phenyl]-5-methyl-4,5-dihydro-3(2H)-pyridazinone,
6-[4-(2-chlorobenzoylamino)-phenyl]-5-methyl-4,5-dihydro-3(2H)-pyridazinone,
6-[4-(4-chlorobenzoylamino)-phenyl]-5-methyl-4,5-dihydro-3(2H)-pyridazinone,
6-[4-(4-bromobenzoylamino)-phenyl]-5-methyl-4,5-dihydro-3(2H)-pyridazinone,
6-[4-(4-fluorobenzoylamino)-phenyl]-5-methyl-4,5-dihydro-3(2H)-pyridazinone,
6-[4-(2,4-dichloro-5-sulfamoylbenzoylamino)-phenyl]-5-methyl-4,5-dihydro-3(2H)-pyridazinone,
6-[4-(4-chloro-3-sulfamoylbenzoylamino)-phenyl]-5-methyl-4,5-dihydro-3(2H)-pyridazinone,
6-[4-(2,4-dichloro-5-sulfamoylbenzoylamino)-phenyl]-4,5-dihydro-3(2H)-pyridazinone,
6-[4-(2-furoylamino)-phenyl]-5-methyl-4,5-dihydro-3(2H)-pyridazinone,
6-[4-(3-furoylamino)-phenyl]-5-methyl-4,5-dihydro-3(2H)-pyridazinone,
6-[4-(2-furoylamino)-phenyl]-4,5-dihydro-3(2H)-pyridazinone,
6-[4-(2-thenoylamino)-phenyl]-4,5-dihydro-3(2H)-pyridazinone,
6-[4-(3-thenoylamino)-phenyl]-5-methyl-4,5-dihydro-3(2H)-pyridazinone,
6-[4-(3-thenoylamino)-phenyl]-4,5-dihydro-3(2H)-pyridazinone,
6-[4-(2-pyridinecarbonylamino)-phenyl]-5-methyl-4,5-dihydro- 3(2H)-pyridazinone,
6-[4-(3-pyridinecarbonylamino)-phenyl]-5-methyl-4,5-dihydro-3(2H)-pyridazinone,
6-[4-(3-pyridinecarbonylamino)-phenyl]-4,5-dihydro-3(2H)-pyridazinone,
6-[4-(4-pyridinecarbonylamino)-phenyl]-4,5-dihydro-3(2H)-pyridazinone,
6-[4-(4-pyridinecarbonylamino)-phenyl]-5-methyl-4,5-dihydro-3(2H)-pyridazinone, and
6-[4-(2-pyridinocarbonylamino)-phenyl]-4,5-dihydro-3(2H)-pyridazinone.

Compounds of the general formula (I) wherein A stands for a radical of (ii) are obtained by reacting a compound of the general formula:

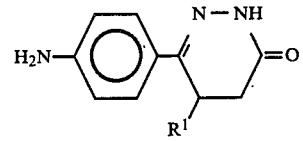 (IV)

(wherein $R^1$ stands for a lower alkyl group), with an amino acid of the general formula:

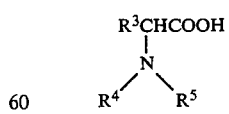

(where $R^3$ stands for a hydrogen atom, a lower alkyl group, a phenyl(lower)alkyl group, a hydroxyphenyl(lower)alkyl group, a lower alkylmercapto(lower)alkyl group, a benzylmercapto(lower)alkyl group, a guanidino(lower)alkyl group, a nitroguanidino(lower)alkyl group, indolyl(lower)alkyl group, a carbamoyl(lower)alkyl group or a carboxy(lower)alkyl group, $R^4$ for a hydrogen atom or a lower alkyl group, $R^5$ for a hydrogen atom, a lower alkyl group, a lower alkanoyl group, a benzoyl group or a benzyloxycarbonyl group, and $R^3$ and $R^4$ may be combined to form a grouping

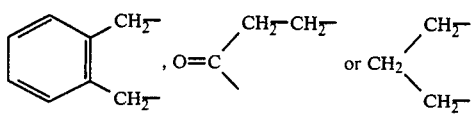

which forms a ring), or a reactive functional derivative thereof.

Compounds of the general formula (V) are easily available as amino acids such as glycine, acetylglycine, N,N-dimethylglycin, N-methylglycin, alanine, phenylalanine, phenylglycin, valine, norvaline, leucin, isoleucin, serine, threonine, methionine, asparagine, aspartic acid, glutamine, glutamic acid, pyroglutamine, arginine, nitroarginine, tryptophan, proline, cystein, tyrosin, methionine, 1,2,3,4-tetrahydroquinoline-2-carboxylic acid, 1,2,3,4-tetrahydroisoquinoline-3-carboxylic acid and S-benzylcystein as well as functional derivative thereof.

In general, a process utilized for peptide synthesis can be applied to the reaction between a compound of the general formula (IV) and the amino acid or a reactive derivative thereof. During this reaction, a proper protecting group is selected and used if protection is necessary for the amino group and side chains of the amino acid under the reaction conditions used.

Mentioned as reactive functional derivatives of the compounds represented by the general formula (V) are acid halides, especially acid chlorides, azides, mixed acid anhydrides such as those with monoalkyl carbonates, and active esters such as p-nitrophenyl esters, 2,4,5-trifluorophenyl esters, N-phthalimide esters and N-oxysuccinimide esters. A compound wherein A is a radical of (ii) can be obtained in a good yield by reacting a compound of the general formula (IV) with such reactive functional derivative.

In case an amino acid itself of the general formula (V) is used, a compound of the general formula (I) can be obtained in a good yield by reacting the amino acid with a compound of the general formula (IV) in the presence of a proper coupling reagent such an N,N-dicyclohexylcarbodiimide or the like. In a compound wherein A is a radical (ii) and $R^5$ is benzyloxycarbonyl group, the NH-bond can easily be regenerated by a usual means for eliminating protective groups, for example, by catalytic reduction with hydrogen and palladium-carbon or by the hydrogen bromide-acetic acid method.

The compounds thus obtained wherein A is a radical (ii) can be converted, if desired, into their physiologically acceptable inorganic salts such as hydrochlorides or organic acid salts such as oxalates, tartarates, etc. in a usual manner.

The compounds wherein A is a radical (ii) have plural asymmetrical carbon atoms. The present invention also involves optical isomers antipodes of these compounds. If resolution of racemates is desired, a compound of the general formula (IV) is optically resolved in a suitable manner and then reacted with a compound of the general formula (V) in d-form or l-form. Otherwise, a compound of the general formula (IV) in racemic form is reacted with one of the optical antipodes of a compound of the general formula (V) to form a diastereomer which is then subjected to optical resolution.

The compounds wherein A is a radical (ii) can be converted, if desired, into their physiologically acceptable proper salts with inorganic acids, such as hydrochlorides and sulfates, or with organic acids, such as oxalates and tartrates, according to a usual method.

Concrete examples of the compound wherein A is a radical (ii) are as follows:

6-[4-(N-carbobenzoxy-L-phenylalanylamino)-phenyl]-5-methyl-4,5-dihydro-3(2H)-pyridazinone, 6-[4-(L-phenylalanylamino)-phenyl]-5-methyl-4,5-dihydro-3(2H)-pyridazinone, 6-(4-acetylglycylaminophenyl)-5-methyl-4,5-dihydro-3(2H)-pyridazinone, 6-[4-(N-carbobenzoxy-D-phenylalanylamino)-phenyl]-5-methyl-4,5-dihydro-3(2H)-pyridazinone, 6-[4-(N-carbobenzoxy-L-alanylamino)phenyl]-5-methyl-4,5-dihydro-3(2H)-pyridazinone, 6-[4-(N-carbobenzoxy-L-tryptophylamino)-phenyl]-5-methyl-4,5-dihydro-3(2H)-pyridazinone, 6-[4-(N-carbobenzoxy-S-benzyl-L-cysteinylaminophenyl]-5-methyl-4,5-dihydro-3(2H)-pyridazinone, 6-[4-(5-oxo-2-pyrrolidinecarbonylamino)-phenyl]-5-methyl-4,5-dihydro-3(2H)-pyridazinone, 6-[4-(2-benzoyl-1,2,3,4-tetrahydroquinoline-3-carbonylamino)-phenyl]-5-methyl-4,5-dihydro-3(2H)-pyridazinone, 6-[4-(N-carbobenzoxy-L-tyrosylamino)-phenyl]-5-methyl-4,5-dihydro-3(2H)-pyridazinone, 6-[4-(N,N-dimethylaminoacetylamino)-phenyl]-5-methyl-4,5-dihydro-3(2H)-pyridazinone, 6-[4-(G-nitro-α-carbobenzoxy-L-arginylamino)-phenyl]-5-methyl-4,5-dihydro-3(2H)-pyridazinone, 6-[4-(N-carbobenzoxy-L-aspartylamino)-phenyl]-5-methyl-4,5-dihydro-3(2H)-pyridazinone, 6-[4-(N-carbobenzoxy-L-asparaginylamino)-phenyl]-5-methyl-4,5-dihydro-3(2H)-pyridazinone, 6-[4-(N-carbobenzoxy-L-prolylamino)-phenyl]-5-methyl-4,5-dihydro-3(2H)-pyridazinone, 6-[4-(N-carbobenzoxy-L-methionylamino)-phenyl]-5-methyl-4,5-dihydro-3(2H)-pyridazinone, 6-[4-(D-phenylalanylamino)-phenyl]-5-methyl-4,5-dihydro-3(2H)-pyridazinone, 6-[4-(L-alanylamino)-phenyl]-5-methyl-4,5-dihydro-3(2H)-pyridazinone, 6-[4-(N-methylaminoacetylamino)-phenyl]-5-methyl-4,5-dihydro-3(2H)-pyridazinone, 6-[4-(L-tryptophenylamino)-phenyl]-5-methyl-4,5-dihydro-3(2H)-pyridazinone, 6-[4-(S-benzyl-L-cysteinylamino)-phenyl]-5-methyl-4,5-dihydro-3(2H)-pyridazinone, 6-[4-(1,2,3,4-tetrahydroisoquinoline-3-carbonylamino)-phenyl]-5-methyl-4,5-dihydro-3(2H)-pyridazinone, 6-(4-L-tyrosylaminophenyl)-5-methyl-4,5-dihydro-3(2H)-pyridazinone, 6-(4-L-arginylaminophenyl)-5-methyl-4,5-dihydro-3(2H)-pyridazinone, 6-(4-L-aspartylaminophenyl)-5-methyl-4,5-dihydro-3(2H)-pyridazinone, 6-(4-L-asparaginylaminophenyl)-5-methyl-4,5-dihydro-3(2H)-pyridazinone, 6-(4-L-prolylaminophenyl)-5-methyl-4,5-dihydro-3(2H)-pyridazinone, 6-(4-L-methionylaminophenyl)-5-methyl-4,5-dihydro-3(2H)-pyridazinone, 6-(4-L-leucylaminophenyl)-5-methyl-4,5-dihydro-3(2H)-pyridazinone, 6-(4-L-glutarylaminophenyl)-5-methyl-4,5-dihydro-3(2H)-pyridazinone, 6-[4-(N-carbobenzoxy-L-glutarylamino)-phenyl]-5-methyl-4,5-dihydro-3(2H)-pyridazinone, 6-[4-(N-carbobenzoxy-L-glutamylamino)-phenyl]-5-methyl-4,5-dihydro-3(2H)-pyridazinone, 6-(4-L-glutamylaminophenyl)-5-methyl-4,5-dihydro-3(2H)-pyridazinone, and 6-(4-phenylglycylaminophenyl)-5-methyl-4,5-dihydro-3(2H)-pyridazinone.

Compounds of the present invention represented by the general formula wherein A is a radical shown by (iii) can be prepared according to various methods among which one usually employed is as follows:

Procedure A:

A compound of the general formula:

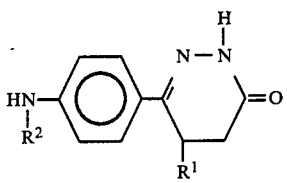
(II)

(wherein $R^1$ and $R^2$ have the same definitions as described above), with an acylating agent of the general formula:

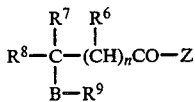
(VI)

(wherein $R^6$, $R^7$, $R^8$, B and n have the same definitions as described above, $R^9$ is a lower alkanoyl group, and Z stands for OH, a chlorine or bromine atom, or a grouping of the formula:

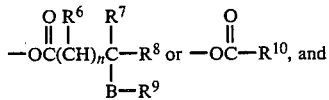

$R^{10}$ stands for a lower alkyl group).

The acylating agent of the general formula (VI) are acid halides such as acid chlorides and acid bromides, its acid anhydride, and its mixed acid anhydrides, for example, those with a monoalkyl carbonate and its active esters such as p-nitrophenyl ester, 2,4,5-trichlorophenyl ester, N-phthalimide ester and N-oxysuccinimide ester.

A compound of the general formula (II) is reacted with such acylating agent of the general formula (VI) in the absence of any solvent or in the presence of a proper solvent, for example, benzene, toluene, xylene, chloroform, dichloromethane, an ether, tetrahydrofuran, dioxane, dimethylformamide, or dimethylsulfoxide, if necessary, by the aid of a suitable base, for example, pyridine, triethylamine, sodium carbonate, potassium carbonate or sodium hydrogen carbonate, for 0.5–5 hours within the temperature range from $-20°$ C. to the boiling point of the reaction mixture.

Procedure B:

A compound of the general formula (II) is reacted with an acylating agent of the general formula (VII):

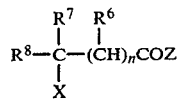
(VII)

(wherein $R^6$, $R^7$, $R^8$ and n have the same definitions as described above, X is a chlorine atom or a bromine atom, Z stands for OH, a chlorine atom, a bromine atom, a grouping

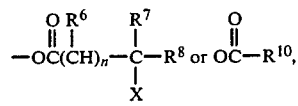

and $R^{10}$ stands for a lower alkyl group), to form a compound of the general formula (VIII):

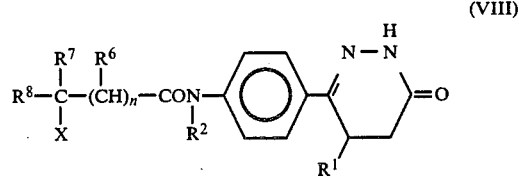
(VIII)

(wherein $R^6$, $R^7$, $R^8$, $R^1$, $R^5$ and n have the same definitions as given above, and X stands for a chlorine or bromine atom), and the compound of the general formula (VIII) is then reacted with a compound of the general formula:

$$R^9\text{---}B\text{---}H \qquad (IX)$$

(wherein $R^9$ is a lower alkanoyl group and B stands for a sulfur atom or an oxygen atom).

The acylating agents of the general formula (VII) are almost the same as those of the general formula (VI) referred to in Procedure (A). This procedure will be described more in detail hereunder. A compound of the general formula (VIII) can be obtained in a good yield by reacting a compound of the general formula (II) with an acylating agent of the general formula(VII), for example, in the form of an acid chloride or bromide, an acid anhydride, a mixed acid anhydride or an active ester, in the absence of any solvent or in the presence of a proper non-reactive solvent, for example, benzene, toluene, dimethylformamide, dimethylsulfoxide, chloroform, dichloromethane, dioxane or tetrahydrofuran, if necessary, with the aid of a base such as pyridine, triethylamine, potassium carbonate, sodium carbonate or sodium hydrogen carbonate, for 0.5–5 hours within the temperature range from $-20°$ C. to the boiling point of the reaction mixture. The compound of the general formula (VIII) is then reacted with a compound of the general formula (IX) in a solvent selected from dimethylformamide, dimethylsulfoxide, an alcohol, water and a mixture thereof in the presence of a suitable acid-binding agent such as potassium carbonate, sodium carbonate, sodium hydrogen carbonate, pyridine or triethylamine for 1–10 hours within the temperature range from $0°$ C. to the boiling point of the reaction mixture, whereby a compound of the general formula (I) can be obtained.

Procedure C:

Compounds wherein $R^9$ is a hydrogen atom can be obtained by hydrolysis of compounds wherein $R^9$ stands for a lower alkanoyl group in a usual manner. This hydrolysis is carried out in methanol, ethanol, water or a mixed solvent of these in the presence of a suitable base, for example, an alkali or alkaline earth metal hydroxide such as sodium hydroxide, potassium hydroxide or barium hydroxide, potassium carbonate or sodium carbonate for 1–5 hours within the temperature range from 0° C. to 100° C., usually at about room temperature, whereby a compound wherein $R^6$ is hydrogen can be obtained easily.

Illustrative of the compounds obtained according to the above procedure are, for example, 6-[4-(3-acetylthio-2-methylpropanoylamino)-phenyl]-5-methyl-4,5-dihydro-3(2H)-pyridazinone, 6-[4-(3-mercpato-2-methylpropanoylamino)-phenyl]-5-methyl-4,5-dihydro-3(2H)-pyridazinone, 6-[4-(3-mercapto-2-ethylpropanoylamino)-phenyl]-5-methyl-4,5-dihydro-3(2H)-pyridazinone, 6-[4-(3-acetylthio-2-propylpropanoylamino)-phenyl]-5-methyl-4,5-dihydro-3(2H)-pyridazinone, 6-[4-(3-acetylthio-2-methylbutanoylamino)-phenyl]-5-methyl-4,5-dihydro-3(2H)-pyridazinone, 6-[4-(3-acetylthio-2-methylpropanoylamino)-phenyl]-4,5-dihydro-3(2H)-pyridazinone, 6-[4-(3-mercapto-2-methylpropanoylamino)-phenyl)-4,5-dihydro-3(2H)-pyridazinone, 6-[4-(2-acetylthiopropanoylamino)-phenyl]-5-methyl-4,5-dihydro-3(2H)-pyridazinone, 6-[4-(2-mercaptopropanoylamino)-phenyl]-5-methyl-4,5-dihydro-3(2H)-pyridazinone, 6-[4-(2-mercaptopropanoylamino)-phenyl)-4,5-dihydro-3(2H)-pyridazinone, 6-[4-(2-mercaptobutanoylamino)-phenyl]-5-methyl-4,5-dihydro- 3(2H)-pyridazinone, 6-[4-(2-mercaptoheptanoylamino)-phenyl]-5-methyl-4,5-dihydro-3(2H)-pyridazinone, 6-[4-(3-mercapto-2-methylpropanoyl-N-methylamino)-phenyl]-5-methyl-4,5-dihydro-3(2H)-pyridazinone, 6-[4-(2-acetoxypropanoylamino)-phenyl]-5-methyl-4,5-dihydro-3(2H)-pyridazinone, 6-[4-(2-hydroxypropanoylamino)-phenyl]-5-methyl-4,5-dihydro-3(2H)-pyridazinone, 6-[4-(3-acetoxypropanoylamino)-phenyl]-5-methyl-4,5-dihydro-3(2H)-pyridazinone, 6-[4-(3-hydroxypropanoylamino)-phenyl]-5-methyl-4,5-dihydro-3(2H)-pyridazinone, 6-[4-(3-acetoxy-2-methylpropanoylamino)-phenyl]-5-methyl-4,5-dihydro-3(2H)-pyridazinone, 6-[4-(3-hydroxy-2-methylpropanoylamino)-phenyl]-5-methyl-4,5-dihydro-3(2H)-pyridazinone, 6-[4-(3-acetoxy-2-methylpropanoylamino)-phenyl]-4,5-dihydro-3(2H)-pyridazinone, 6-[4-(3-hydroxy-2-methylpropanoylamino)-phenyl]-4,5-dihydro-3(2H)-pyridazinone, 6-[4-(2-acetoxypropanoylamino)-phenyl]-4,5-dihydro-3(2H)-pyridazinone, 6-[4-(2-hydroxypropanoylamino)-phenyl]-4,5-dihydro-3(2H)-pyridazinone, 6-[4-(N-methyl-2-hydroxypropanoylamino)-phenyl]-5-methyl-4,5-dihydro-3(2H)-pyridazinone, 6-[4-(N-methyl-2-acetoxypropanoylamino)-phenyl]-5-methyl-4,5-dihydro-3(2H)-pyridazinone, 6-[4-(N-butyl-2-acetoxypropanoylamino)-phenyl]-5-methyl-4,5-dihydro-3(2H)-pyridazinone, 6-[4-(2-acetoxybutanoyl)-phenyl]-5-methyl-4,5-dihydro-3(2H)-pyridazinone, 6-[4-(2-hydroxybutanoylamino)-phenyl]-5-methyl-4,5-dihydro-3(2H)-pyridazinone, and 6-[4-(2-hydroxyheptanoylamino)-phenyl]-5-methyl-4,5-dihydro-3(2H)-pyridazinone.

All of the compounds concerned with the present invention are new substances and exhibit excellent pharmacological activities such as strong blood pressure depressing activity, platelets aggregation inhibiting activity and myocardial-contraction reinforcing activity.

The following experimental results have been obtained for platelets aggregation inhibiting activity and anti-hypersentive activity exhibited by the compounds with the present invention.

(1) Platelets aggregation inhibiting activity:

The influence on aggregation of platelets was examined according to the Born's method[1]. Blood extracted by inserting a cannula into the carotid artery of a rabbit under non-anesthetic conditions was mixed with a 3.8% solution of sodium citrate in a ratio of 9:1 and the mixture was subjected to centrifugal action for 10 minutes at 1100 r.p.m., using a laboratory centrifugal separator, whereby red blood corpuscles were precipitated to yield a platelets-rich plasma (referred to hereinafter simply as PRP). A small amount of PRP was placed in a cubette of Aglygometer and stirred with a small stirrer. To this were added successively a solution of a substance to be tested (pH 7.4, physiologically isotonic) and collagen to initiate aggregation of platelets. The difference in transmission of PRP in the process of aggregation was continuously recorded. The amount of collagen added for initiating the aggregation was set to a minimum amount enabling observation of the maximum aggregation. The strength of inhibiting the aggregation by the substance to be tested was calculated from the concentration of the substance to be tested which exhibited the same inhibiting effect as shown by $10^{-4}$M aspirin. Designation of the aggregation-ihibiting activity:— (no inhibiting effect), ± (weaker in the aggregation-inhibiting activity than aspirin), + (equivalent to aspirin), ++ (below 10 times as much as aspirin), +++ (below 100 times as much as aspirin), and ++++ (above 100 times as much as aspirin).

Reference[1]. G. V. R. Born, Nature, 194, 927 (1962).

(2) Anti-hypertensive activity:

After the development of hypertension in rats of at least 20 week-old, spontaneously hypertensive rats (SHR) were starved for 17 hours and used for the test. The sistolic blood pressure of the tail artery was measured by an indirect method under non-anesthetic conditions before administration of a medicament and 1, 2, 4, 6 and 24 hours after administration of the medicament. The substance to be tested was dissolved or suspended in a 0.2% CMC solution and orally administered to a group consisting of 3–5 rats showing a sistolic blood pressure of 180 mmHg or higher. The results of the experiments made for the compounds of this invention according to the above mentioned methods is shown in Table 1 (in the table, A stands for classification of the compounds corresponding to the definition of A in the above general formula).

TABLE 1

| A | Example No. | Dosage (mg/Kg) | Sistolic blood pressure in average (mmHg) | | | | | Platelets aggregation inhibiting activity |
|---|---|---|---|---|---|---|---|---|
| | | | 0 | 2 | 4 | 6 | 24 (hr) | |
| (i) | 1 | 4 | 212 | 215 | 210 | 210 | — | +++ |
| | 3 | 4 | 222 | 180 | 180 | 182 | 207 | +++ |
| | 5 | 4 | 183 | 116 | 121 | 140 | 170 | +++ |
| | 6 | 4 | 215 | 212 | 210 | 212 | — | + |
| | 7 | 4 | 185 | 188 | 185 | 188 | — | +++ |
| | 8 | 4 | 217 | 184 | 185 | 195 | 214 | +++ |
| (ii) | 11 | 4 | 207 | 164 | 164 | 164 | 184 | +++ |
| | 12 | 4 | 220 | 162 | 162 | 165 | 200 | +++ |
| | | 1 | 220 | 190 | 197 | 203 | 222 | |
| | 13 | 4 | 220 | 178 | 172 | 173 | 192 | + |
| | 16 | 4 | 193 | 163 | 160 | 152 | 171 | +++ |
| | 19 | 4 | 198 | 192 | 201 | — | — | +++ |
| | 14 | 4 | 197 | 132 | 140 | 134 | 162 | +++ |
| | 18 | 4 | 192 | 129 | 129 | 127 | 159 | +++ |
| (iii) | 29 | 4 | 197 | 152 | 159 | 167 | 189 | +++ |
| | 30 | 4 | 207 | 152 | 154 | 152 | 202 | +++ |
| | 31 | 4 | 203 | 143 | 146 | 156 | 201 | +++ |
| | 32 | 4 | 213 | 183 | 181 | 186 | 201 | +++ |
| | 33 | 4 | 180 | 130 | 135 | 140 | 175 | ++++ |
| | 34 | 4 | 182 | 125 | 135 | 134 | 170 | ++++ |
| *1 | Hydrazine | 4 | 188 | 154 | 165 | 174 | 173 | + |

*1 Control

Given below are examples of the present invention.

EXAMPLE 1

6-[4-(2-hydroxybenzoylamino)-phenyl]-5-methyl-4,5-dihydro-3(2H)-pyridazinone 1.2 Grams (7.7 m-mol) of salicyloyl chloride and 1.0 g (4.9 m-mol) of 6-(p-aminophenyl)-5-methyl-4,5-dihydro-3(2H)-pyridazinone in 10 ml of benzene were stirred for 6 hours at 50° C. After cooling, the resultant crystals were washed with benzene and recrystallized from methanol-water whereby 750 mg of the title compound was obtained. M.P. 218°–220° C.

EXAMPLE 2

6-(4-thenoylaminophenyl)-5-methyl-4,5-dihydro-3(2H)-pyridazinone

A mixture of 1.1 g of 2-thenoyl chloride, 1.0 g of 6-(p-aminophenyl)-5-methyl-4,5-dihydro-3(2H)-pyridazinone and 10 ml of benzene was treated in the same manner as described in Example 1 to effect reaction whereby 800 mg of the title compound was obtained. M.P. 256°–258° C.

EXAMPLES 3–7

The following compounds were obtained according to the same operation as described in Example 1 from the corresponding carboxylic acid chlorides and the corresponding pyridazinone compounds.

(Example 3)

6-[4-(3-pyridinecarbonylamino)-phenyl]-5-methyl-4,5-dihydro- 3(2H)-pyridazinone, M.P. 243°–245° C.

(Example 4)

6-[4-(4-pyridinecarbonylamino)-phenyl]-5-methyl-4,5-dihydro-3(2H)-pyridazinone, M.P. 288°–290° C.

(Example 5)

6-[4-(2-pyridinecarbonylamino)-phenyl]-5-methyl-4,5-dihydro-3(2H)-pyridazinone, M.P. 227°–228° C.

(Example 6)

6-[4-(4-chloro-3-sulfamoylbenzoylamino)phenyl]-5-methyl-4,5-dihydro-3(2H)-pyridazinone, M.P. 316°–319° C.

(Example 7)

6-[4-(2,4-dichloro-3-sulfamoylbenzoylamino)phenyl]-5-methyl-4,5-dihydro-3(2H)-pyridazinone, M.P. 267°–270° C.

EXAMPLE 8

6-[4-(2-furoylamino)phenyl]-5-methyl-4,5-dihydro-3(2H)-pyridazinone

In 20 ml of dichloromethane was dissolved 0.56 g (5 m-mol) of 2-furancarboxylic acid. To this solution was added 0.7 ml of triethylamine, and the mixture was cooled to −20° C. Next, 0.65 ml of isobutyl chloroformate was added to the mixture and the whole was stirred for 30 minutes at a temperature from −10° C. to −20° C. To this mixture was added a dimethylformamide solution containing 1.0 g (4.9 m-mol) of 6-(p-aminophenyl)-5-methyl-4,5-dihydropyridazinone. After removing the ice bath, the mixture was stirred for 3 hours at room temperature and the solvent was then distilled off under reduced pressure. Water was added to the residue and a solid material was collected by filtration. The solid material was washed with water and dichloromethane and then recrystallized from methanol-water whereby 570 mg of the title compound was obtained. M.P. 213°–216° C.

EXAMPLE 9

6-[4-(2-acetoaminobenzoylamino)-phenyl]-5-methyl-4,5-dihydro-3(2H)-pyridazinone

Using 1.3 g (7.26 m-mol) of N-acetylanthranilic acid, 20 ml of dimethylformamide, 1.01 ml of triethylamine and 0.94 ml of isobutyl chloroformate, the operation was carried out in the same manner as described in Example 8 to form a mixed acid anhydride. Using this mixed acid anhydride and 1.0 g (4.92 m-mol) of 6-(p-aminophenyl)-5-methyl-4,5-dihydro-3(2H)-pyridazinone in 20 ml of dimethylformamide, the reaction was carried out almost in the same operation as described in Example 8 whereby the title compound was obtained as a crude product, which was purified by way of column chromatography on silica gel (solvent: benzene, acetic acid and methanol of 10:3:0.6). 750 Milligrams of the pure title compound was thus obtained. M.P. 226°–228° C.

EXAMPLE 10

6-[4-(2-acetoxybenzoylamino)-phenyl]-5-methyl-4,5-dihydro-3(2H)-pyridazinone

To 1.4 g (7.77 m-mol) of acetylsalicylic acid were added 2 ml of thionyl chloride and 5 ml of benzene, and the mixture was stirred for 3 hours under reflux. After allowing the mixture to stand for cooling, the mixture was concentrated under reduced pressure until dryness. To the residue were added 10 ml of benzene and 1.0 g (4.92 m-mol) of 6-(p-aminophenyl)-5-methyl-4,5-dihydro-3(2H)-pyridazinone, and the mixture was stirred for 1.5 hours under reflux. After cooling, the precipitated crystals were collected by filtration and washed successively with benzene and water. When the crystals were dissolved in a mixed solvent of benzene, acetic acid and methanol (10:3:0.6) and the solution was allowed to stand, crystals were precipitated which were removed by filtration. The filtrate was concentrated and the residue was recrystallized from methanol-water whereby 400 mg of the title compound was obtained. This was in the form of an amorphous powder.

IR-spectra (KBr tablets): 1760, 1670, 1600, 1520, 1340, 1190 and 840 cm$^{-1}$ (characteristic absorption bands).

EXAMPLE 11

6-[(4-N-carbobenzoxy-L-phenylalanyl)-aminophenyl]-5-methyl-4,5-dihydro-3(2H)-pyridazinone In 20 ml of dry methylene chloride were dissolved 1.5 g of N-carbobenzoxy-L-phenylalanine and 0.7 g of triethylamine, and the solution was cooled to −20° C. To this solution was added 0.65 ml of isobutyl chloroformate, and the mixture was reacted for 30 minutes at a temperature from −15° C. to −10° C. To this mixture was added 1.0 g of 6-(p-aminophenyl)-5-methyl-4,5-dihydro-3(2H)-pyridazinone in 20 ml of dry dimethylformamide at −20° C., and the mixture was reacted for 2 hours at room temperature. The reaction mixture was concentrated under reduced pressure and water was added to the residue to precipitate crystals. The resultant crystals were recrystallized from methanol-water whereby 1.91 g of the end product was obtained. M.P. 187°-189° C.

EXAMPLE 12

6-[4-(L-phenylalanyl)-aminophenyl]-5-methyl-4,5-dihydro-3(2H)-pyridazinone

In 10 ml of a 25% acetic acid solution of hydrogen bromide was dissolved at room temperature 1.0 g of the compound obtained in Example 11, and the solution was allowed to stand for 90 minutes. To this reaction mixture was added a large amount of ether. The resultant crystals were collected by filtration, treated with an aqueous solution of sodium hydrogen carbonate and washed with water and methanol to obtain 400 mg of the end product. M.P. 191°-196° C.

EXAMPLE 13

6-(4-acetylglycylaminophenyl)-5-methyl-4,5-dihydro-3(2H)-pyridazinone

A mixed acid anhydride was prepared from 0.58 g of acetylglycin under the almost same conditions as described in Example 11 and then reacted with 6-(p-aminophenyl)-5-methyl-4,5-dihydropyridazinone to obtain the end product. Recrystallization from dimethylformamide and water afforded 410 mg of the end product. M.P. 260° C. or higher.

The following compounds were obtained in a similar manner:

EXAMPLE 14

6-[4-(N-carbobenzoxy-D-phenylalanyl)-aminophenyl]-5-methyl-4,5-dihydropyridazinone, M.P. 180°-183° C.

EXAMPLE 15

6-[4-(N-carbobenzoxy-L-alanyl)-aminophenyl]-5-methyl-4,5-dihydro-3(2H)-pyridazinone, M.P. 192°-194° C.

EXAMPLE 16

6-[4-(N-carbobenzoxy-L-tryptophyl)-aminophenyl]-5-methyl-4,5-dihydro-3(2H)-pyridazinone, amorphous powder, IR-absorption spectra (KBr tablets, cm$^{-1}$): 1670, 1610, 1520, 1410, 1340, 1180, 740 and 700.

EXAMPLE 17

6-[4-(N-carbobenzoxy-S-benzyl-L-cysteinyl)-aminophenyl]-5-methyl-4,5-dihydro-3(2H)-pyridazinone, amorphous powder, IR-absorption specta (KBr tablets, cm$^{-1}$): 3260, 1660, 1600, 1510, 1340, 1235, 1030 and 692.

EXAMPLE 18

6-[4-(5-oxo-2-pyrrolidinecarbonyl)-aminophenyl]-5-methyl-4,5-dihydro-3(2H)-pyridazinone, M.P. 310°-312° C. (with decomp.).

EXAMPLE 19

6-[4-(2-benzoyl-1,2,3,4-tetrahydroisoquinoline-3-carbonyl)-aminophenyl]-5-methyl-4,5-dihydro-3(2H)-pyridazinone, M.P. 198°-200° C.

EXAMPLE 20

6-[4-(N-carbobenzoxy-L-tyrosyl)-aminophenyl]-5-methyl-4,5-dihydro-3(2H)-pyridazinone, amorphous powder, IR-absorption spectra (KBr tablets, cm$^{-}$): 1680, 1520, 1420, 1360, 1250 and 840.

EXAMPLE 21

6-[4-(N,N-dimethylaminoacetyl)-aminophenyl]-5-methyl-4,5-dihydro-3(2H)-pyridazinone In 1 ml of water was dissolved 0.7 g of N,N-dimethylglycin hydrochloride. This solution was mixed with a solution of 1.0 g of 6-(p-aminophenyl)-5-methyl-4,5-dihydro-3(2H)-pyridazinone in 20 ml of dimethylformamide. To this mixture was added under ice-cooling 1.2 g of dicyclohexylcarbodiimide, and the reaction was effected for 2 hours. The reaction mixture was allowed to stand for 2 days in a cool place and concentrated under reduced pressure. Water was added to the residue and any insoluble matter was eliminated by filtration. Sodium hydrogen carbonate was added to the filtrate to make it alkaline whereby crystals were precipitated which were then recrystallized from methanol-water to obtain 950 mg of the end product. M.P. 195°-197° C.

EXAMPLE 22

6-[4-(G-nitro-α-carbobenzoxy-L-arginyl)-aminophenyl]-5-methyl-4,5-dihydro-3(2H)-pyridazinone The title compound was obtained by reacting the corresponding G-nitro-α-carbobenzoxy-L-arginine with 6-(p-aminophenyl)-5-methyl-4,5-dihydro-3(2H)-pyridazinone in a manner similar to that described in Example 21. Amorphous powder, IR-absorption spectra (KBr tablets, cm$^{-1}$): 1680, 1520, 1410, 1340, 1260, 1030 and 840.

EXAMPLE 23

6-[4-(N-carbobenzoxy-L-aspart)-aminophenyl]-5-methyl-4,5-dihydro-3(2H)-pyridazinone In 10 ml of methanol was dissolved 1.5 g of the corresponding β-benzyl ester derivative. To this solution was added at room temperature 10 ml of 1-N caustic soda to effect hydrolysis. The mixture was treated in a usual

EXAMPLE 24

6-[4-(N-carbobenzoxy-L-asparaginyl)-aminophenyl]-5-methyl-4,5-dihydro-3(2H)-pyridazinone In 0.8 ml of pyridine, 1.4 ml of N-ethylpyridine and 8 ml of chloroform was dissolved 2.66 g of N-carbobenzoxy-L-asparagine. To this solution was added dropwise under cooling at −10° C. a solution of 1.2 g of pivalic chloride in 2 ml of chloroform. The mixture was reacted for 20 minutes at 0°–10° C. After cooling the mixture again at −10° C., a solution of 2.03 g of 6-(p-aminophenyl)-5-methyl-4,5-dihydro-3(2H)-pyridazinone in 5 ml of dimethylformamide was added to the mixture and the whole was reacted for 30 minutes at room temperature to obtain 1.28 g of the end product. Amorphous powder, IR-absorption spectra (KBr tablets, cm$^{-1}$): 3280, 1650, 1522, 1405, 1320 and 1258.

EXAMPLE 25

6-[4-(N-carbobenzoxy-L-prolyl)-aminophenyl]-5-methyl-4,5-dihydro-3(2H)-pyridazinone The title compound was obtained in the same manner as described in Example 24.

EXAMPLE 26

6-[4-(N-carbobenzoxy-L-methyionyl)-aminophenyl]-5-methyl-4,5-dihydro-3(2H)-pyridazinone An active ester was prepared from N-carbobenzoxy-L-methionine and trifluorophenol and added to a solution of 1.0 g of 6-(p-aminophenyl)-5-methyl-4,5-dihydro-3(2H)-pyridazinone in dimethylformamide. The mixture was reacted for 3 hours at 50°–60° C. and for additional 3 hours at 100° C. The solvent was distilled off under reduced pressure and the residue was purified by column chromatography on silica gel (solvent: benzene and acetic acid in a ratio of 10:3) whereby 1.1 g of an amorphous powder was obtained. IR-absorption spectra (KBr tablets, cm$^{-1}$): 1670, 1520, 1410, 1340, 1250, 1180 and 1040.

EXAMPLE 27

6-[4-(D-phenylalanyl)-aminophenyl]-5-methyl-4,5-dihydro-3(2H)-pyridazinone

The title compound was obtained by subjecting the compound obtained in Example 14 to reaction in the same manner as described in Example 12. M.P. 192°–197° C.

EXAMPLE 28

6-[4-(L-alanyl)-aminophenyl]-5-methyl-4,5-dihydro-3(2H)-pyridazinone

The title compound was obtained by subjecting the compound obtained in Example 15 to reaction in the same manner as described in Example 12. M.P. 222°–223° C.

EXAMPLE 29

6-[4-(3-acetylthio-2-methylpropanoylamino)-phenyl]-5-methyl-4,5-dihydro-3(2H)-pyridazinone A mixture of 2.0 g of 6-(p-aminophenyl)-5-methyl-4,5-dihydro-3(2H)-pyridazinone, 2.1 g of 3-acetylthio-2-methylpropanoyl chloride, 0.92 g of pyridine and 20 ml of benzene was reacted for 30 minutes under reflux. The solvent was distilled off under reduced pressure and the reaction mixture was purified by column chromatography on silica gel (solvent: benzene, acetic acid and methanol in a ratio of 10:3:0.6) whereby 2.25 g of the end product was obtained. IR-absorption spectra (KBr tablets, cm$^{-1}$): 3280, 1680, 1620, 1540, 1360 and 960.

EXAMPLE 30

6-[4-(3-mercapto-2-methylpropanoylamino)-phenyl]-5-methyl-4,5-dihydro-3(2H)-pyridazinone In 20 ml of aqueous methanol was dissolved 1.0 g of the compound obtained in Example 29. To this solution was added 10 ml of 1-N caustic soda solution at room temperature in a stream of nitrogen, and the mixture was reacted for 3 hours. The mixture was then made acidic by the addition of 6-N hydrochloric acid and extracted with methylene chloride. The methylene chloride phase was dried over anhydrous sodium sulfate and the solvent was distilled off. Benzene was added to the residue for crystallization to obtain 750 mg (yield: 85.3%) of the end product. M.P. 215°–217° C. (uncorrected). IR-absorption spectra (KBr tablets, cm$^{-1}$): 3100, 2520, 1670, 1610, 1530, 1340 and 1180.

EXAMPLE 31

6-[4-(2-acetylthiopropanoylamino)-phenyl]-5-methyl-4,5-dihydro-3(2H)-pyridazinone To 20 ml of N,N-dimethylformamide were added 0.54 g of thioacetic acid, 0.98 g of anhydrous potassium carbonate and then 2.0 g of 6-[4-(α-bromopropionylamino)-phenyl]-5-methyl-4,5-dihydro-3(2H)-pyridazinone, and the mixture was reacted for 2 hours at room temperature. The mixture was further reacted for 1 hour after the addition of 2 ml of water. Insoluble matters were removed from the mixture by filtration and the filtrate was concentrated under reduced pressure to obtain a crude end product which was then purified by column chromatography on silica gel (solvent: benzene, acetic acid and methanol in a ratio of 10:3:0.6) whereby 1.8 g of the purified end product was obtained. Amorphous powder. IR-absorption spectra (KBr tablets, cm$^{-1}$): 3275, 1680, 1540, 1350, 1040 and 840.

EXAMPLE 32

6-[4-(2-mercaptopropanoylamino)-phenyl]-5-methyl-4,5-dihydro-3(2H)-pyridazinone

In 20 ml of methanol was dissolved 1.0 g of the compound obtained in Example 31. To this solution was added in a stream of nitrogen 10 ml of 1N caustic soda solution, and the mixture was reacted for 90 minutes at room temperature. The mixture was made acidic by the addition of 6-N hydrochloric acid to precipitate crystals, which were then collected by filtration and washed with methanol to obtain 750 mg of the end product. M.P. 236°–237° C. (uncorrected).

EXAMPLE 33

6-[4-(2-acetoxypropanoylamino)-phenyl]-5-methyl-4,5-dihydro- 3(2H)-pyridazinone

In 45 ml of dichloromethane was dissolved 2.0 g of α-acetoxypropionic acid. To this solution was added 2.1 ml of triethylamine and the mixture was cooled at −20° C. To this mixture was added dropwise 1.95 ml of isobutyl chloroformate and the mixture was reacted for 30 minutes at a temperature from −10° C. to −20° C. To the mixture was then added a solution of 3.0 g of 6-(p-

(manner whereby 300 ml of the end product was obtained. M.P. 177° C. (with decomp.).)

aminophenyl)-5-methyl-4,5-dihydro-3(2H)-pyridazinone in 20 ml of dimethylformamide, and the mixture was reacted for 90 minutes at room temperature. After the solvent was distilled off under reduced pressure, water was added to the residue and the whole was extracted with dichloromethane. The solvent was distilled off and the residue was purified by column chromatography on silica gel (solvent: benzene-acetic acid-methanol in a ratio of 10:3:0.6) whereby 2.7 g of the end product was obtained.

IR-absorption spectra (KBr tablets, cm$^{-1}$): 1740, 1680, 1540, 1350, 1240, 1040 and 840.

EXAMPLE 34

6-[4-(2-hydroxypropanoylamino)-phenyl]-5-methyl-4,5-dihydro-3(2H)-pyridazinone

In 30 ml of methanol was dissolved 1.0 g of the compound obtained in Example 33. To this solution was added at room temperature 10 ml of 1-N caustic soda solution, and the mixture was reacted for 2 hours. The mixture was made acidic by the addition of 6-N hydrochloric acid and concentrated under reduced pressure to a smaller volume whereby an oily substance was precpitated and solidified, which was then collected by filtration and washed with water to obtain 700 mg of the end product. M.P. 224°–233° C. (uncorrected).

We claim:

1. A pyridazinone derivative of the formula:

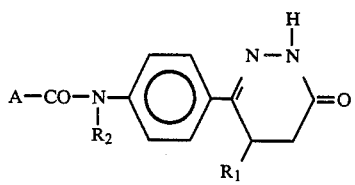

wherein $R^1$ stands for a hydrogen atom or a methyl group; $R^2$ for a hydrogen atom or a lower alkyl group; and A for a grouping of the formula:

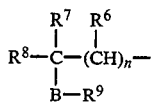

wherein $R^6$, $R^7$ and $R^8$ each stand for a hydrogen atom or a lower alkyl group, B is an oxygen atom or a sulfur atom, $R^9$ stands for a hydrogen atom or a lower alkanoyl group, and n is 0 or 1.

2. A physiologically acceptable salt of the compound according to claim 1.

3. A method for treating circulatory conditions comprising administering to a patient an effective blood pressure depressing, platelet aggregation inhibiting or myocardial-contraction reinforcing amount of a compound according to claim 1.

4. A pyridazinone derivative of the formula:

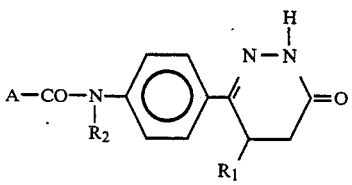

wherein $R^1$ stands for a hydrogen atom or a methyl group; $R^2$ for a hydrogen atom or a lower alkyl group; and A for (i) a ring selected from a benzene ring, a furan ring, a thiophene ring and a pyridine ring (on which ring 1–3 substituents or atoms selected from amino groups, nitro groups, lower alkanoylamino groups, hydroxyl groups, lower alkanoyloxy groups, sulfamoyl groups and halogen atoms may be present), or (iii) a grouping of the formula:

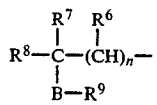

(wherein $R^6$, $R^7$ and $R^8$ each stand for a hydrogen atom or a lower alkyl group, B is an oxygen atom or a sulfur atom, $R^9$ stands for a hydrogen atom or a lower alkanoyl group, and n is 0 or 1).

5. A physiologically acceptable salt of the compound according to claim 4.

6. The compound according to claim 4, which is 6-(4-(2-hydroxybenzoylamino)-phenyl)-5-methyl-4,5-dihydro-3(2H)-pyridazinone.

7. The compound according to claim 4, which is 6-(4-(3-pyridinecarbonylamino)-phenyl)-5-methyl-4,5-dihydro-3(2H)-pyridazinone.

8. The compound according to claim 4, which is 6-(4-(4-pyridinecarbonylamino)-phenyl)-5-methyl-4,5-dihydro-3(2H)-pyridazinone.

9. The compound according to claim 4, which is 6-(4-(2-pyridinocarbonylamino)-phenyl)-5-methyl-4,5-dihydro-3(2H)-pyridazinone.

10. The compound according to claim 4, which is 6-(4-(2,4-dichloro-3-sulfamoylbenzoylamino)-phenyl)-5-methyl-4,5-dihydro-3(2H)-pyridazinone.

11. The compound according to claim 4, which is 6-(4-(2-furoylamino)-phenyl)-5-methyl-4,5-dihydro-3(2H)-pyridazinone.

12. The compound according to claim 4, which is 6-(4-(3-acetylthio-2-methylpropanoylamino)-phenyl)-5-methyl-4,5-dihydro-3(2H)-pyridazinone.

13. The compound according to claim 4, which is 6-(4-(3-mercapto-2-methylpropanoylamino)-phenyl)-5-methyl-4,5-dihydro-3(2H)-pyridazinone.

14. The compound according to claim 4, which is 6-(4-(2-acetylthiopropanoylamino)-phenyl)-5-methyl-4,5-dihydro-3(2H)-pyridazinone.

15. The compound according to claim 4, which is 6-(4-(2-mercaptopropanoylamino)-phenyl)-5-methyl-4,5-dihydro-3(2H)-pyridazinone.

16. The compound according to claim 4, which is 6-(4-(2-acetoxypropanoylamino)-phenyl)-4,5-dihydro-3(2H)-pyridazinone.

17. The compound according to claim 4, which is 6-(4-(2-hydroxypropanoylamino)-phenyl)-5-methyl-4,5-dihydro-3(2H)-pyridazinone.

18. A physiologically acceptable salt according to claim 30, wherein said compound is a member selected from the group consisting of 6-(4-(2-hydroxybenzoylamino)-phenyl)-5-methyl-4,5-dihydro-3(2H)-pyridazinone, 6-(4-(3-pyridinecarbonylamino)-phenyl)-5-methyl-4,5-dihydro-3(2H)-pyridazinone, 6-(4-(4-pyridinecarbonylamino)-phenyl)-5-methyl-4,5-dihydro-3(2H)pyridazanone, 6-(4-(2-pyridinocarbonylamino)-phenyl)-5-methyl-4,5-dihydro-3(2H)-pyridazinone, 6-(4-(2,4-dichloro-3-sulfamoylbenzoylamino)-phenyl)-5- methyl-4,5-dihydro-3(2H)-pyridazinone and 6-(4-(2-furoylamino)-phenyl)-5-methyl-4,5-dihydro-3(2H)-pyridazinone.

19. A physiologically acceptable salt according to claim 5, wherein said compound is a member selected from the group consisting of 6-(4-(3-acetylthio-2-methylpropanoylamino)-phenyl)-5-methyl-4,5-dihydro-3(2H)-pyridazinone, 6-(4-(3-mercapto-2-methylpropanoylamino)-phenyl)-5-methyl-4,5-dihydro-3(2H)-pyridazinone, 6-(4-(2-acetylthiopropanoylamino)-phenyl)-5-methyl-4,5-dihydro-3(2H)-pyridazinone, 6-(4-(2-mercaptopropanoylamino)-phenyl)-5-methyl-4,5-dihydro-3(2H)-pyridazinone, 6-(4-(2-acetoxypropanoylamino)-phenyl)-5-methyl-4,5-dihydro-3(2H)-pyridazinone, and 6-(4-(2-hydroxypropanoylamino)-phenyl)-5-methyl-4,5-dihydro-3(2H)-pyridazinone.

20. A method according to claim 22, wherein said compound is a member selected from the group consisting of 6-(4-(2-hydroxybenzoylamino)-phenyl)-5-emthyl-4,5-dihydro-3(2H)-pyridazinone, 6-(4-(3-pyridinecarbonylamino)-phenyl)-5-methyl-4,5-dihydro-3(2H)-pyridazinone, 6-(4-(4-pyridinecarbonylamino)-phenyl)-5-methyl-4,5-dihydro-3(2H)-pyridazinone, 6-(4-(2-pyridinocarbonylamino)-phenyl)-5-methyl-4,5-dihydro-3(2H)-pyridazinone, 6-(4-(2,4-dichloro-3-sulfamoylbenzoylamino)-phenyl)-5-methyl-4,5-dihydro-3(2H)-pyridazinone and 6-(4-(2-furoylamino)-phenyl)-5-methyl-4,5-dihydro-3(2H)-pyridazinone.

21. A method according to claim 22, wherein said compound is a member selected from the group consisting of 6-(4-(3-acetylthio-2-methylpropanoylamino)-phenyl)-5-methyl-4,5-dihydro-3(2H)-pyridazinone, 6-(4-(3-mercapto-2-methylpropanoylamino)-phenyl)-5-methyl-4,5-dihydro-3(2H)-pyridazinone, 6-(4-(2-acethylthiopropanoylamino)-phenyl)-5-methyl-4,5-dihydro-3(2H)-pyridazinone, 6-(4-(2-mercaptopropanoylamino)-phenyl)-5-ethyl-4,5-dihydro-3(2H)-pyridazinone, 6-(4-(2-acetoxypropanoylamino)-phenyl)-5-methyl-4,5-dihydro-3(2H)-pyridazinone, and 6-(4-(2-hydroxypropanoylamino)-phenyl)-5-methyl-4,5-dihydro-3(2H)-pyridazinone.

22. A method for treating circulatory conditions comprising administering to a patient an effective blood pressure depressing, platelet aggregation inhibiting or myocardial-contraction reinforcing amount of a compound according to claim 4.

* * * * *